United States Patent
Mohajeri

(10) Patent No.: US 9,597,675 B2
(45) Date of Patent: *Mar. 21, 2017

(54) OXIDATION CATALYSTS ON ALKALINE EARTH SUPPORTS

(71) Applicant: University of Central Florida Research Foundation, Inc., Orlando, FL (US)

(72) Inventor: Nahid Mohajeri, Rockledge, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 316 days.
This patent is subject to a terminal disclaimer.

(21) Appl. No.: 14/198,030

(22) Filed: Mar. 5, 2014

(65) Prior Publication Data
US 2014/0187410 A1    Jul. 3, 2014

Related U.S. Application Data

(60) Division of application No. 13/588,779, filed on Aug. 17, 2012, now Pat. No. 8,652,993, and a
(Continued)

(51) Int. Cl.
*B01J 23/00* (2006.01)
*B01J 31/28* (2006.01)
(Continued)

(52) U.S. Cl.
CPC .......... *B01J 31/28* (2013.01); *B01D 53/9445* (2013.01); *B01J 23/44* (2013.01); *B01J 23/50* (2013.01);
(Continued)

(58) Field of Classification Search
CPC ... B01J 31/28; B01J 23/58; B01J 23/66; B01J 37/0209; B01J 23/60; B01J 37/0201; B01J 31/069; B01J 23/44; B01J 27/053; B01J 23/50; B01J 23/52; B01J 35/0006; B01J 21/063; B01J 37/0213; B01J 35/0013;
(Continued)

(56) References Cited

U.S. PATENT DOCUMENTS 2,922,783 A * 1/1960 Kuhn .................. C07H 5/06
                                                        536/53
3,007,941 A * 11/1961 Copelin .............. C07D 307/36
                                                        502/243
(Continued)

FOREIGN PATENT DOCUMENTS

EP        2128227 A1 * 12/2009  .......... C07D 307/42

*Primary Examiner* — Colleen Dunn
*Assistant Examiner* — Haytham Soliman
(74) *Attorney, Agent, or Firm* — Jetter & Associates, P.A.

(57) ABSTRACT

An oxidation catalyst includes a support including particles of an alkaline earth salt, and first particles including a palladium compound on the support. The oxidation catalyst can also include precious metal group (PMG) metal particles in addition to the first particles intermixed together on the support. A gas permeable polymer that provides a continuous phase can completely encapsulate the particles and the support. The oxidation catalyst may be used as a gas sensor, where the first particles are chemochromic particles.

19 Claims, 3 Drawing Sheets

Related U.S. Application Data continuation-in-part of application No. 14/062,312, filed on Oct. 24, 2013, now Pat. No. 8,703,642.

(60) Provisional application No. 61/524,937, filed on Aug. 18, 2011.

(51) Int. Cl.

| | | |
|---|---|---|
| *B01J 23/44* | (2006.01) | |
| *B01J 23/50* | (2006.01) | |
| *B01J 23/52* | (2006.01) | |
| *B01J 27/053* | (2006.01) | |
| *B01J 31/06* | (2006.01) | |
| *B01J 23/58* | (2006.01) | |
| *B01J 23/60* | (2006.01) | |
| *B01J 23/66* | (2006.01) | |
| *B01J 37/02* | (2006.01) | |
| *B01D 53/94* | (2006.01) | |
| *B01J 35/00* | (2006.01) | |
| *B01J 21/06* | (2006.01) | |
| *B01J 23/42* | (2006.01) | |
| *B01J 23/63* | (2006.01) | |
| *B01J 35/02* | (2006.01) | |
| *G01N 27/12* | (2006.01) | |
| *G01N 33/00* | (2006.01) | |

(52) U.S. Cl.
CPC .............. *B01J 23/52* (2013.01); *B01J 23/58* (2013.01); *B01J 23/60* (2013.01); *B01J 23/66* (2013.01); *B01J 27/053* (2013.01); *B01J 31/069* (2013.01); *B01J 37/0201* (2013.01); *B01J 37/0209* (2013.01); *B01D 2255/102* (2013.01); *B01D 2255/104* (2013.01); *B01D 2255/106* (2013.01); *B01D 2255/1023* (2013.01); *B01D 2255/2042* (2013.01); *B01D 2255/20707* (2013.01); *B01D 2255/20715* (2013.01); *B01J 21/063* (2013.01); *B01J 23/42* (2013.01); *B01J 23/63* (2013.01); *B01J 35/0006* (2013.01); *B01J 35/0013* (2013.01); *B01J 35/023* (2013.01); *B01J 37/0213* (2013.01); *G01N 27/125* (2013.01); *G01N 33/005* (2013.01); *Y02T 10/22* (2013.01)

(58) Field of Classification Search
CPC .......... B01J 35/023; B01J 23/63; B01J 23/42; B01D 53/9445; B01D 2255/20707; B01D 2255/102; B01D 2255/104; B01D 2255/2042; B01D 2255/1023; B01D 2255/20715; B01D 2255/106; Y02T 10/22; G01N 33/005; G01N 27/125
See application file for complete search history.

(56) References Cited

U.S. PATENT DOCUMENTS

| | | |
|---|---|---|
| 3,935,157 A | 1/1976 | Schiller et al. |
| 5,849,073 A | 12/1998 | Sakamoto et al. |
| 7,446,939 B2 | 11/2008 | Sharma et al. |
| 2006/0216496 A2 | 9/2006 | Gray et al. |
| 2007/0224081 A1 | 9/2007 | Bokerman et al. |

* cited by examiner

OXIDATION CATALYSTS ON ALKALINE EARTH SUPPORTS

CROSS REFERENCE TO RELATED APPLICATIONS

This application is a continuation-in-part (CIP) of U.S. non-provisional patent application Ser. No. 14/062,312 entitled "METHOD OF FORMING SUPPORTED DOPED PALLADIUM CONTAINING OXIDATION CATALYSTS" filed on Oct. 24, 2013, now U.S. Pat. No. 8,703,642, which is a divisional application and claims the benefit of U.S. non-provisional patent application Ser. No. 13/588,779 entitled "DOPED PALLADIUM CONTAINING OXIDATION CATALYSTS" filed on Aug. 17, 2012, now U.S. Pat. No. 8,652,993, which claims the benefit of Provisional Application Ser. No. 61/524,937 entitled "DOPED PALLADIUM CONTAINING OXIDATION CATALYSTS", filed Aug. 18, 2011, which is herein incorporated by reference in its entirety.

U.S. GOVERNMENT RIGHTS

This invention was made with U.S. Government support under Florida Hydrogen Initiative contract #DEFC 3604GO14225 awarded by the U.S. Department of Energy. The Government has certain rights in this invention.

FIELD

Disclosed embodiments relate to catalysts or gas sensors on support particles.

BACKGROUND

One of the future alternatives to current fossil-based transportation fuels has been centered on hydrogen gas ($H_2$). Currently, $H_2$ is the primary energy source of today's space exploration projects (e.g., as rocket propellant). It is also used in fuel cells that power a variety of machinery including automobiles. Furthermore, $H_2$ is an important industrial commodity produced and used in many industries. For example, it is used for the reduction of metal oxides (e.g. iron ore), ammonia synthesis, and production of hydrochloric acid, methanol and higher alcohols, aldehydes, hydrogenation of various petroleum, coal, oil shale and edible oils, among others. However, $H_2$ is a colorless, odorless gas, and is also a flammable gas with a lower explosive limit of about 4% in air. Therefore reliable $H_2$ sensors are required to detect $H_2$ leaks wherever $H_2$ is produced, stored, or used.

To detect $H_2$ sensors comprising a palladium alloy Schottky diode formed on a silicon substrate are known. These sensors are based on metal-oxide-semiconductor (MOS) technology that is used in the semiconductor industry. The gas sensing MOS structures comprise a $H_2$-sensitive metal (palladium or its alloy) on a dielectric (e.g., an oxide) adherent to a semiconductor. This $H_2$ sensor has been commercialized and exploited for detecting $H_2$ leaks during pre-launches of space vehicles. Others have also used palladium or the like as a sensing element for detecting $H_2$. A $H_2$ sensor containing an array of micromachined cantilever beams coated with palladium/nickel has also been disclosed.

Semiconductors with wide band-gap (e.g. gallium nitride) have also been used to make diodes for $H_2$ detection. One of the concerns for all of these types of sensors using palladium or the like is the requirement of a high operating temperature (greater than 200° C.) and further elevated temperatures (greater than 500° C.) to reactivate the sensing element, bringing about lengthy analysis. Another issue is sensitivity of the sensing element to unintended compounds that are commonly found in the atmosphere, including water vapor, various hydrocarbons, and various reducing gases such as carbon monoxide and hydrogen sulfide. Although not conventionally used, chemochromic $H_2$ sensors are known. Some chemochromic $H_2$ sensors lack field stability and have a tendency to crack and peel and some can be washed off by precipitation and/or condensation. Moreover, some chemochromic $H_2$ sensors do not show selectivity to $H_2$.

Thus, there remains a need for an improved, reliable and durable chemochromic $H_2$ sensor, or more generally an oxidation catalyst for a chemochromic reducing gas sensor or catalyst, for a variety of applications, including space, transportation, oil refineries, and chemical plants.

SUMMARY

This Summary is provided to introduce a brief selection of disclosed concepts in a simplified form that are further described below in the Detailed Description including the drawings provided. This Summary is not intended to limit the claimed subject matter's scope.

An oxidation catalyst comprises a support comprising particles of at least one alkaline earth metal salt, and first particles comprising a palladium compound on the support. Alkaline earth metals include beryllium (Be), magnesium (Mg), calcium (Ca), strontium (Sr), barium (Ba), and radium (Ra), and they are recognized by disclosed embodiments to all have similar chemical properties having the same outer state electron configuration.

As used herein, a "support" refers to an alkaline earth metal salt material in which the first particles and optional precious metal group (PMG) second particles are deposited onto in the formation of the oxidation catalyst. The alkaline earth metal salt support can be in layer form on another layer, such as a layer comprising a plurality of bound particles on a solid surface (e.g., on a wall), or be in a discrete particle form.

The particles on the support can comprise only the first particles comprising a single Pd composition, such as PdO. Alternatively, the first particles (e.g., PdO) can be intermixed with PGM second particles (e.g., Pt). The PMG metal can comprise gold, silver or one of the platinum group metals including platinum.

Disclosed alkaline earth metal salt particle supported oxidation catalysts can be used as a pigment for hydrogen sensing/detection or other sensing/detection of other reducing gases where they may be encapsulated in a reducing gas permeable polymer matrix such as silicone rubber or silicone resin. In this embodiment, the first particles comprise chemochromic particles. In another embodiment, the oxidation catalyst is used as a catalyst without polymer encapsulation. In oxidation catalyst embodiments, the first particles need not comprise chemochromic particles.

DETAILED DESCRIPTION

Figure 1A:
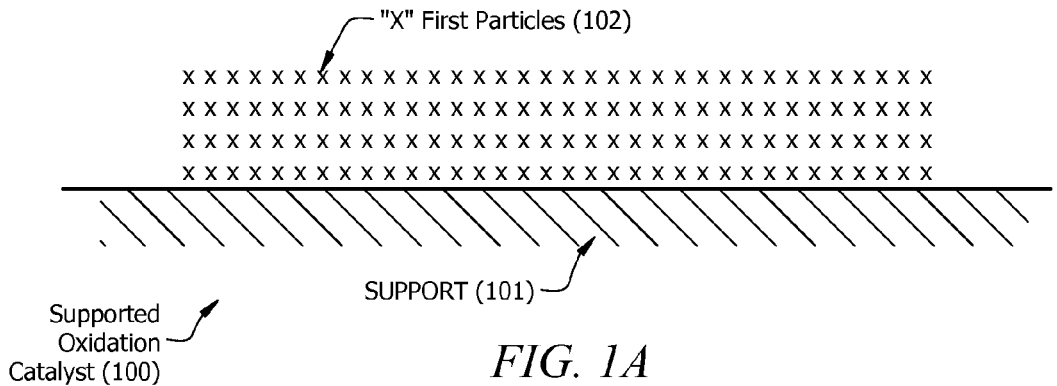
FIG. 1A is a cross sectional depiction of an example oxidation catalyst comprising a support including particles of an alkaline earth metal salt and first particles comprising a palladium compound on the support, according to an example embodiment.
Figure 1B:
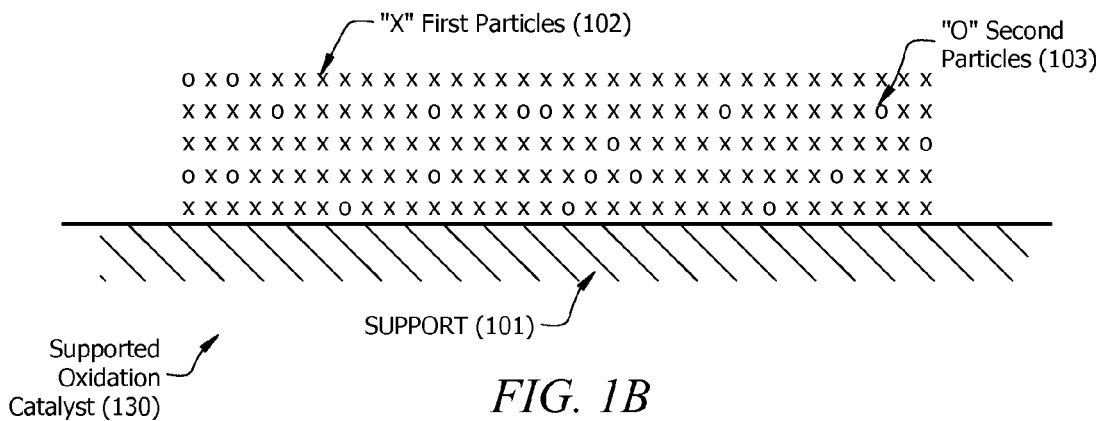
FIG. 1B is a cross sectional depiction of an example oxidation catalyst comprising a support comprising particles of an alkaline earth metal salt, and mixed particles on the support including first particles comprising a palladium compound and second particles comprising a PMG metal, according to an example embodiment.
Figure 1C:
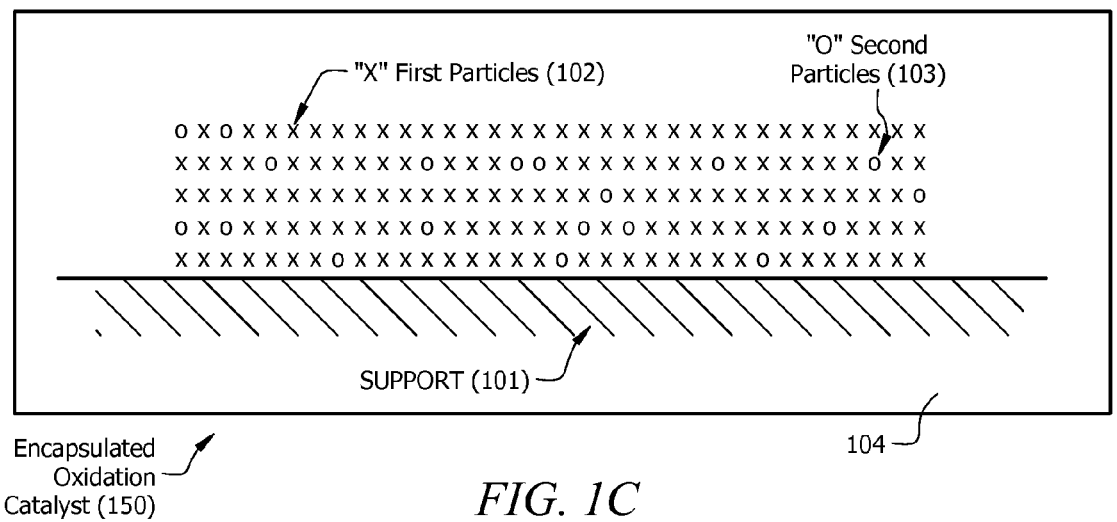
FIG. 1C is a cross sectional depiction of an example encapsulated oxidation catalyst comprising the oxidation catalyst in FIG. 1B along with an optional reducing gas permeable polymer that forms a continuous phase which provides complete encapsulation for the alkaline earth salt support particles and the and mixed particles, according to an example embodiment.

Disclosed embodiments in this Disclosure are described with reference to the attached figures, wherein like reference numerals are used throughout the figures to designate similar or equivalent elements. FIGS. 1A-C are not drawn to scale, and they are provided merely for illustration. Several aspects are described below with reference to example applications for illustration.

It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Disclosed embodiments include alkaline earth metal salt particle supports which provide significantly improved catalyst performance including kinetics and detection sensitivity over conventional titania supports. One example alkaline earth support is a BaSO$_4$ support. However, the alkaline earth support material can generally include all other alkaline earth elements (Be, Mg, Ca, Sr, or Ra), and can be in forms other than sulfate, such as carbonate, hydroxide, oxide, or sulfide.

Some disclosed embodiments are based on the discovery that a palladium compound oxidation catalyst such as PdO on a support when "doped" with particles comprising a PMG metal provides supported oxidation catalysts which oxidize a reducing gas (e.g., hydrogen, carbon monoxide, or hydrocarbons) with oxidation kinetics sped up significantly and sensitivity increased significantly as compared to the palladium compound (e.g., PdO) on the support alone. Disclosed alkaline earth metal salt particle supports (e.g., BaSO$_4$) may be combined with doping of the palladium compound (e.g., PdO) with a PMG metal, which as evidenced in the Examples below may further improve oxidation kinetics and detection sensitivity of the oxidation catalyst.

In the "doped" embodiments, the PMG metal particles feature the metal being in its atomic/elemental form which may be clearly contrasted with metal in metal compounds, such as compounds selected from the group consisting of oxides, hydroxides and hydrated oxides of platinum group metals. As well known in metallurgy, physics and chemistry, an elemental (or atomic) metal is in its elemental uncharged state while metals in metal compounds are in an ionic (generally cationic) state. For example, for the conventional PdO pigment, Pd is in the +2 state (Pd$^{+2}$), and as known in the art, and upon exposure to a reducing gas such as $H_2$, Pd$^{+2}$ reduces to its elemental/atomic form Pd$^0$ which results in a visible color change (and the generation of water). An elemental metal such as Pd$^0$ cannot itself accept electrons.

The support is generally selected so that interaction of the metal particles with the surface of support surfaces minimizing the total energy required for palladium compound (e.g., PdO) reduction. This suggests a small chemical interaction between support and the metal particles and hence destabilization of the palladium compound particles on the surface of the support, such as the PMG metal "dopant" (e.g. Pt) lowering the activation energy required for PdO reduction.

Disclosed supported oxidation catalysts embodied as chemochromic sensors (pigments) change color in a presence of at least one reducing gas. Embodied as chemochromic reducing gas sensors, disclosed reducing gas sensors are irreversible sensors.

The response time of disclosed chemochromic reducing gas sensors toward $H_2$ gas by including nanosized PMG dopant particles with palladium compound particles (e.g., PdO) has been found to unexpectedly be decreased by about 10 fold while encapsulated in a silicone resin. As noted above, disclosed supported oxidation catalysts can also be used as catalysts, such as to reduce undesirable emissions from fossil fuel powered vehicles. Moreover, as also noted above, use of disclosed alkaline earth metal salt particle supports provide further improvement in catalyst or reducing gas function including both kinetics and detection sensitivity.

FIG. 1A is a cross sectional depiction of an example oxidation catalyst 100 comprising a support 101 comprising particles of an alkaline earth metal salt, and at least first particles 102 being particles comprising a palladium compound on the support 101, according to an example embodiment. For gas detection applications, the first particles 102 comprise chemochromic particles.

Although the support 101 is shown in FIG. 1A in layer form, such as comprising a polycrystalline layer, the support 101 may also be in discrete particle form. Typically the support 101 comprises alkaline earth metal salt particles which are generally colorless, white, or slightly colored.

In one embodiment, the support 101 comprises alkaline earth metal salt particles having a size in a range from 0.1 µm to 1.0 µm, and in one particular embodiment from 0.2 µm to 0.25 µm for pigment applications to maximize opacity.

The first particles 102 can comprise palladium oxide, palladium hydroxide, or a palladium salt. The first particles 102 can have a median size in the range of 2 nm to 8 nm.

In typical applications, the supported oxidation catalyst 100 can be adhered to a substrate where it can provide its chemochromic reducing gas sensing or catalyst function, such as on a metal surface (e.g. a metal wall). The shapes of the support 101, first particles 102 and optional second particles 103 shown in FIGS. 1B and 1C are arbitrary.

FIG. 1B is a cross sectional depiction of an example supported oxidation catalyst 130 comprising a support 101 comprising particles of an alkaline earth metal salt, first particles 102 comprising a palladium compound (e.g., PdO), and optional second particles 103 comprising a PMG metal, on the support 101, according to an example embodiment. Disclosed PMG's can include gold, silver, or platinum group metals, such as ruthenium, rhodium, osmium, iridium, and platinum.

In one embodiment the second particles 103 have a median size in the range from 5 nm to 10 nm. The relative concentration ratio of the second particles 103 to first particles 102 can range from 1:10 to 1:25 by weight.

Disclosed supported oxidation catalysts can further comprise an ultraviolet (UV) absorber or UV Blocker, or a mixture thereof to remedy possible adverse environmental effects. The UV blocker can comprise $ZnO_2$ or $TiO_2$. The UV absorber can comprise compounds from the triazine family, such as benzotriazol or a benzopheneone. The UV absorber or UV Blocker can be in the range of 1-10 wt. % of the supported oxidation catalyst. Although not shown in FIGS. 1A-C, UV absorber or UV Blocker particles if shown would be on the support 101 analogous to first particles 102 or second particles 103 (FIG. 1B), or can be physically mixed with the oxidation catalyst.

FIG. 1C is a depiction of an example encapsulated supported oxidation catalyst 150, according to an example embodiment. Encapsulated supported oxidation catalyst 150 comprises the oxidation catalyst 130 comprising a support 101 including the alkaline earth metal salt particles shown in FIG. 1B along with an optional reducing gas permeable polymer 104 that forms a continuous phase (matrix) which provides complete encapsulation for the alkaline earth metal salt particles and mixed particles comprising first particles 102 and optional second (PGM metal) particles 103.

The gas permeable polymer 104 continuous phase can be formed by admixing a suitable material, such as a moisture curable or heat curable silicone sealant with dry catalyst particles or its slurry comprising alkaline earth metal salt particles which will be the support 101, first particles (palladium compound) 102, and optional second particles of PMG metal 103 in a liquid phase before drying. Upon curing the silicone sealant a rubbery gas permeable silicone polymer forms a continuous phase that provides complete encapsulation as shown in FIG. 1C.

In some embodiments, the supported oxidation catalyst can comprise a composite layer. A composite layer is known in the material arts and is defined herein as a composite engineered material made from two or more constituent materials with significantly different physical or chemical properties which remain separate and distinct on a macroscopic level within the finished structure. In principle, composites can be constructed of any combination of two or more materials, metallic, organic, or inorganic; but the constituent forms are typically more restricted. The matrix provided by the gas permeable polymer 104 is the body constituent, acting as a continuous phase having the other materials referred to as the additive phases embedded therein, with the gas permeable polymer 104 serving to enclose the other composite components and give it bulk form.

Disclosed embodiments also include methods of forming disclosed oxidation catalysts. A support is provided, such as comprising a plurality of alkaline earth metal salt particle particles. First particles comprising a palladium compound (e.g., PdO) and optionally second particles comprising a PMG metal are deposited on the alkaline earth metal salt particle support(s) in a liquid phase slurry including a solvent to form nanosized palladium compound (e.g., PdO) particles and PMG metal particles. A solid-liquid separation process such as filtering the slurry allows removal of the liquid phase to form dried solid supported oxidation catalyst which may be referred to as composite particles.

The depositing can comprise co-depositing the first particles comprising the palladium compound and the optional PMG metal particles using a precursor for the palladium compound and a precursor for the PMG metal. As described below, depositing the palladium compound after depositing the PMG metal under reflux condition may provide enhanced sensing performance.

In one embodiment for gas sensing or detection, the method further comprises admixing a moisture curable silicone sealant with the particles in the liquid phase, and then curing the moisture curable silicone sealant to form a rubbery gas permeable silicone polymer. In this embodiment, the gas permeable polymer provides a continuous phase that completely encapsulates the first particles comprising the palladium compound, the second particles comprising the PMG metal, and the alkaline earth metal salt particle supports (see FIG. 1C described above).

As noted above, disclosed supported oxidation catalysts can be used in a variety of applications including in the development of chemochromic passive sensors for detecting reducing gases such as hydrogen, carbon monoxide, and hydrocarbons (e.g., natural gas or propane). These gases/liquids are widely used and produced in many industries and a safe operation is a top priority for all of them. Disclosed alkaline earth metal salt particle supported oxidation catalysts can also provide a layer of protection against accidental releases of these gases and therefore reinforces a safe manufacturing/utilization environment. Furthermore, disclosed supported oxidation catalysts can be used as catalysts in the automotive industry to reduce hydrocarbon, carbon monoxide, and NOx emissions, or in any industry that carry methane combustion such as natural gas-powered vehicles. Other example applications include depollution of natural gas-powered vehicles, and catalytic processes for energy production from natural gas.

The effectiveness of gas sensors, such as disclosed supported oxidation catalysts used as chemochromic reducing gas sensors, is typically evaluated by measuring the time necessary to reach a given level of color change, and by determining the total amount of color change. The latter is expressed as ΔE and is measured by a colorimeter. ΔE measures a difference in color by measuring specific parameters of the film (L, a, b). These parameters refer to a color system for measuring absolute chromaticity, L*a*b* and color difference Δ(L*a*b*) or ΔE. Color is defined in three dimensions: hue, chroma (saturation) and lightness. L*=the gradient from light to dark, a*=the gradient from red to green, and b*=the gradient from yellow to blue, and $\Delta E^* = \{(\Delta L^*)^2 + (\Delta a^*)^2 + (\Delta b^*)^2\}^{1/2}$. This equation gives a standard measurement technique by which one can compare color changes from different chemochromic reducing gas sensor film samples. The greater the ΔE* value, the greater the color contrast. Chemochromic reducing gas sensor films can be analyzed both before and after exposure to the reducing gas, allowing quantification of the intensity of the color change.

EXAMPLES

Disclosed embodiments are further illustrated by the following specific Examples, which should not be construed as limiting the scope or content of this Disclosure in any way. For example, although the alkaline earth supports are described in the Examples as being $BaSO_4$ supports, alkaline earth supports can generally include all other alkaline earth elements and be in forms other than sulfate, such as carbonate, hydroxide, oxide, or sulfide. Moreover, as noted above, although Pt is generally used as the "dopant" in these examples, Pt can be replaced by gold, silver, or another PGM other than Pt.

Example methods of preparation of disclosed supported oxidation catalysts are now described. Samples referred to as "base" in FIGS. 2-3 such as PK-1-135 NM1 and PK-2-50-NM1-1 respectively, described below refer to known PdO on $TiO_2$ support controls (no Pt doping). For testing, the samples were all placed inside a vial and were exposed to 100% $H_2$ gas with a 45 ml/min flow rate. The Examples are all based on 10 g batches of support ($TiO_2$ or $BaSO_4$) except for the large scale batches of support which were 250 g batches.

Example 1

Depositing 0.3 Wt. % PT Doping onto PdO/$TiO_2$ by Reflux

Example 1A

To deposit PdO particles on $TiO_2$ (titania), a slurry of 2.5 g $TiO_2$ in 100 mL water was adjusted to pH 10.6 using 12 M NaOH and stirred at 70° C. for an hour. 2.5 mL of 0.281M $PdCl_2$ solution in 2 M HCl was added dropwise to the mixture, taking care to keep the solution at pH 10.6 using 12 M NaOH. Once all the $PdCl_2$ solution was added, the pH of the mixture was adjusted to 8 using 3 M HCl. This mixture was stirred and heated for an hour while the PdO was deposited onto surfaces of the titania. The resulting PdO/$TiO_2$ solid product was then filtered, washed thoroughly with water, and dried under vacuum at 200° C. for 3 hours. The PdO/$TiO_2$ solid product was used to provide the PK-1-135 NM1 controls.

Example 1B 0.019 g $Na_2PtCl_6$ was added to a slurry of 2.5 g PdO/$TiO_2$ in 100 mL DI water. 0.027 g sodium citrate was added to the mixture, which was then placed under reflux at 70° C. and stirred overnight (~16 hours). The Pt on PdO/$TiO_2$ solid product was filtered, washed thoroughly with water and dried under vacuum at room temperature to provide a disclosed supported oxidation catalysts identified as PK-1-136-NM13.

Figure 2:
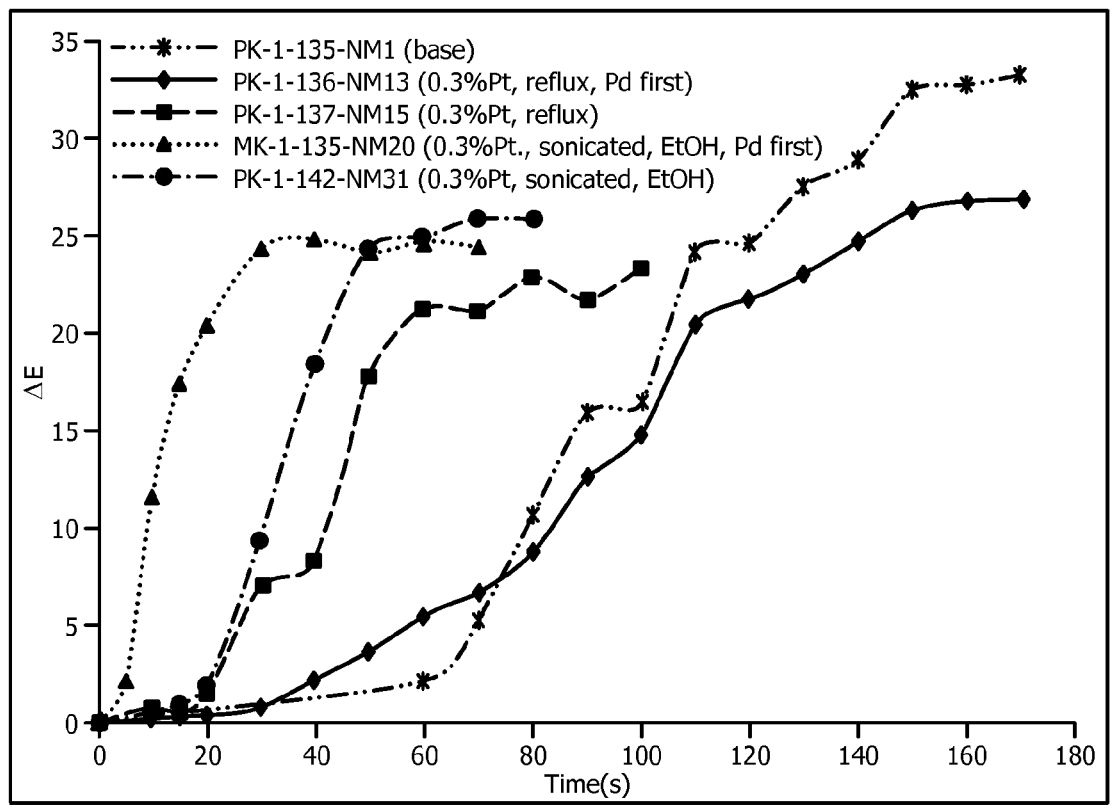
FIG. 2 shows $\Delta E$ vs. exposure time to 100% $H_2$ gas sensing performance for various disclosed platinum-doped Pd/TiO$_2$ supported oxidation catalysts used as pigments encapsulated in DOW 734® silicone resin that were synthesized as compared to a known PdO on TiO$_2$ control (no Pt doping).

FIG. 2 which shows ΔE vs. exposure time to 100% $H_2$ gas for various disclosed Pt doped PdO/$TiO_2$ supported oxidation catalysts used as pigments encapsulated in DOW 734® silicone resin, along with PK-1-135 NM1 ("Base") for a PdO on $TiO_2$ control. The performance of PK-1-136-NM13 can be seen to be similar to PK-1-135 NM1.

PK-1-137-NM15 was prepared by reversing the order of steps 1A and 1B. First Pt was deposited onto a $TiO_2$ support (Step 1B) and then PdO was deposited onto Pt/$TiO_2$ by following step 1A (its ΔE vs. exposure time to 100% $H_2$ gas is shown in FIG. 2). PK-1-137-NM15 can be seen to provide a significant performance enhancement compared to the PK-1-135 NM1 "base" control and PK-1-136-NM13.

Example 2

Depositing 0.3 Wt % Pt onto a PdO/$TiO_2$ Support by Sonication

Example 2A

To deposit PdO, a slurry of 2.5 g $TiO_2$ in 100 mL water was adjusted to pH 10.6 using 12 M NaOH and stirred at 70° C. for an hour. 2.5 mL of 0.281M $PdCl_2$ solution in 2 M HCl was added dropwise to the mixture, taking care to keep the solution at pH 10.6 using 12 M NaOH. Once all the $PdCl_2$ solution was added, the pH of the mixture was adjusted to 8 using 3 M HCl. This mixture was stirred and heated for an hour while the PdO was deposited onto surfaces of the titania. The solid PdO/$TiO_2$ product was filtered, washed thoroughly with water and dried at room temperature.

Example 2B

Then, 0.019 g $Na_2PtCl_6$ was added to a slurry of 2.5 g PdO/$TiO_2$ in 100 mL ethanol to give a loading of 0.3 wt % Pt on the support. The pH of the solution was adjusted to 6 using 12 M NaOH. Sonication was carried out on the reaction mixture using a direct immersion titanium tip (20 kHz, 100 W $cm^{-2}$) at room temperature. Sonication uses applied sound energy to agitate particles in the sample. The resulting solid Pt on PdO/$TiO_2$ product was filtered, thoroughly washed with ethanol, dried at room temperature and then baked at 200° C. for 3 hrs to provide PK-1-135-NM-20 (its ΔE vs. exposure time to 100% $H_2$ gas is shown in FIG. 2). PK-1-135-NM-20 can be seen to provide a significant performance enhancement compared to the PK-1-135 NM1 "base" control.

PK-1-142-NM31 was prepared by reversing the order of steps 2A and 2B. First, Pt was deposited onto a $TiO_2$ support (Step 2B), and then PdO was deposited onto Pt/$TiO_2$ by following step 2A (its ΔE vs. exposure time to 100% $H_2$ gas is shown in FIG. 2). PK-1-142-NM31 can also be seen to provide a significant performance enhancement compared to the PK-1-135 NM1 "base" control.

Example 3

Synthesis of an Irreversible BaSO$_4$/PdO 3 Wt % PdO Chemochromic Pigment (BaSO$_4$ Supports)

A slurry of 2.5 g BaSO$_4$ in 100 mL water was adjusted to pH 10.6 using 12 M NaOH and stirred at 70 C for an hour. 2.5 mL of 0.281M PdCl$_2$ solution in 2 M HCl was added dropwise to the mixture, taking care to keep the solution at pH 10.6 using 12 M NaOH. Once all the PdCl$_2$ solution was added, the pH of the mixture was adjusted to 7 using 3 M HCl. This mixture was stirred and heated for an hour while the PdO was deposited onto the surfaces of the BaSO$_4$. The solid product was filtered, washed thoroughly with water and dried under vacuum at 110° C. for 3 hours to provide PK-2-124-NM48C-1 (shown in FIG. 3). The catalyst PK-2-142-NM55 (shown in FIG. 3) was synthesized by adding ethanol to PK-1-124-NM48C-1 and sonicating the slurry using a direct immersion titanium tip (20 kHz, 100 W cm$^{-2}$) at room temperature.

Example 4

Exposure of PdO/BaSO$_4$ Pigments (BaSO$_4$ Supports)

Figure 3:
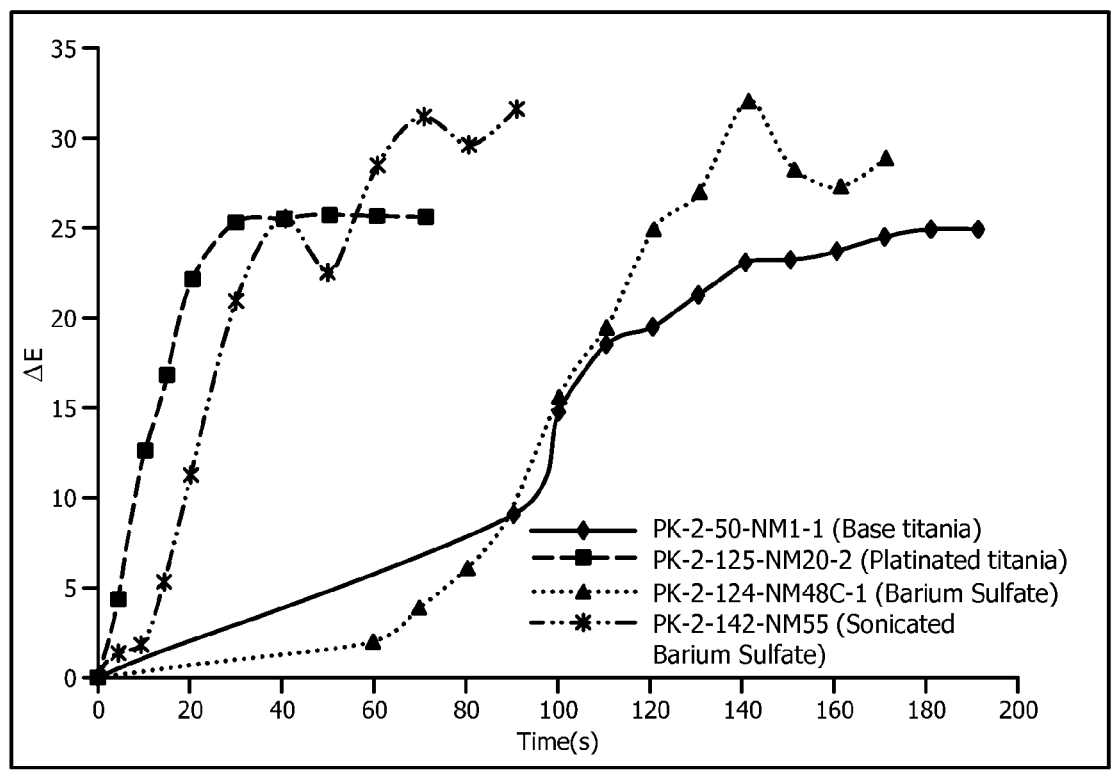
FIG. 3 shows $\Delta E$ vs. exposure time to 100% $H_2$ sensing gas for various disclosed PdO/BaSO$_4$ oxidation catalysts (BaSO$_4$ as supports) used as pigments encapsulated in DOW 734® silicone resin that were synthesized as compared to a known ("base") PdO on TiO$_2$ oxidation catalyst control (no Pt doping).

FIG. 3 shows ΔE vs. exposure time performance for two synthesized PdO/BaSO$_4$ pigments (see PK-2-124-NM48C-1 and PK-2-142-NM55 in FIG. 3) encapsulated in DOW 734 silicone resin. PK-2-142-NM55 can be seen in FIG. 3 to provide a significant performance enhancement compared to the PK-2-50 NM1-1 "base" titania support control. The PdO/BaSO$_4$ oxidation catalysts prepared by sonication (30 kHz) showed a response time curve very similar to the disclosed Pt doped PdO/TiO$_2$ catalyst shown as PK-2-125-NM-20-2. The BaSO$_4$ supported catalyst thus eliminated the need for the PMG metal dopant, and therefore will be comparatively more cost effective. However, as noted above, BaSO$_4$ can be used with PMG metal dopants for even faster kinetics.

Example 5

Depositing 0.3 Wt % Pt onto a PdO/BaSO$_4$ Support by Sonication

To deposit PdO, a slurry of 10 g BaSO$_4$ in 100 mL water was adjusted to pH 10.6 using 2.56 M NaOH and stirred at 70° C. for one hour. 10 mL of 0.28 M PdCl$_2$ solution in 2 M HCl was added dropwise to the mixture, taking care to keep the solution at pH 10.6 using 2.56 M NaOH. Once all the PdCl$_2$ solution was added, the pH of the mixture was adjusted to 7 using 2 M HCl. This mixture was stirred and heated for one hour while the PdO was deposited onto the surfaces of the BaSO$_4$. The solid PdO/BaSO$_4$ was filtered, washed thoroughly with ethanol, dried at room temperature overnight, and dried at room temperature in a vacuum oven for one hour. Then, 4 mL of 0.02 M Na$_2$PtCl$_6$ was added to a slurry of 5 g PdO/BaSO$_4$ in 100 mL ethanol to give a loading of 0.3 wt % Pt onto the support. Sonication was carried out on the reaction mixture using a direct immersion titanium top (30 kHz, 100 W cm$^{-2}$) at room temperature. The solid Pt on PdO/BaSO$_4$ product was filtered, thoroughly washed with ethanol, dried at room temperature overnight, dried at room temperature in a vacuum oven for one hour, and baked at 110° C. for 3 hours to form a disclosed supported oxidation catalyst including Pt doped PdO on a BaSO$_4$ support.

Example 6

Synthesis of Large Scale Irreversible BaSO$_4$/PdO 3 Wt % PdO Chemochromic Pigment (BaSO$_4$ Supports)

Example 6A

To deposit PdO particles on BaSO$_4$, a slurry of 250 g BaSO$_4$ (a "large scale" batch of supports) in 2000 mL water was adjusted to pH 10.6 using 2.56 M NaOH and stirred at 70° C. for one hour. 250 mL of 0.28 M PdCl$_2$ in 2 M HCl and 250 mL 2.56 M NaOH was added to the mixture by automated injection, taking care to keep the solution at pH 10.6 using 2.56 M NaOH or 2 M HCl. Once all the PdCl$_2$ and NaOH was added, the pH of the mixture was adjusted to pH 7 using 2M HCl. This mixture was stirred and heated for one hour while the PdO was deposited onto the surfaces of the BaSO$_4$. The solid PdO/BaSO$_4$ product was filtered, washed thoroughly with ethanol, dried at room temperature overnight, and dried at room temperature in a vacuum oven for one hour.

Example 6B

A slurry of the product from Example 6A in 1000 mL ethanol was sonicated using a direct immersion titanium tip (60 kHz, 100 W cm$^{-2}$) at room temperature. The solid PdO/BaSO$_4$ product was filtered, thoroughly washed with ethanol, dried at room temperature overnight, and dried in a vacuum oven at room temperature for one hour. The product was then baked at 110° C. for 3 hours. The large scale batch produced evidences the scalability of the disclosed barium sulfate supported pigment.

Example 6C

The product from Example 6A was baked at 110° C. for 3 hours. Then a slurry of the product in 1000 mL ethanol was sonicated using a direct immersion titanium tip (60 kHz, 100 W cm$^{-2}$) at room temperature. The solid PdO/BaSO$_4$ product was filtered, thoroughly washed with ethanol, dried at room temperature overnight, and dried in a vacuum oven at room temperature for one hour.

Figure 4:
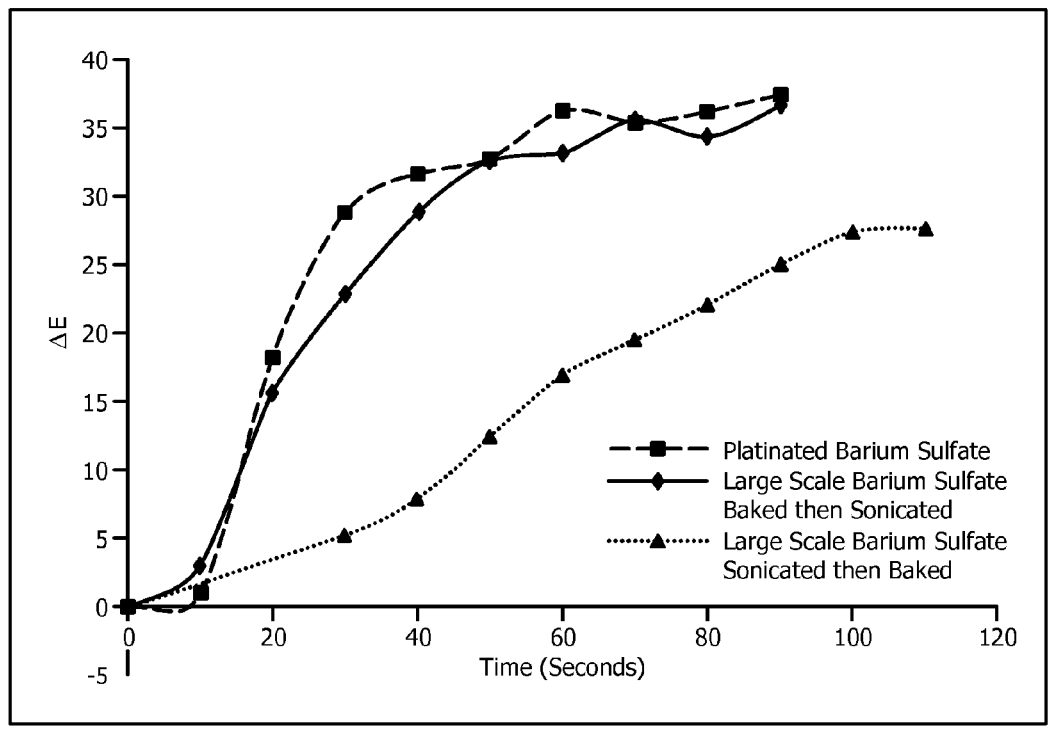
FIG. 4 shows $\Delta E$ vs. exposure time to 100% $H_2$ sensing gas for disclosed embodiments including platinated BaSO$_4$, large scale batch barium sulfate that was baked before sonication, and large scale batch barium sulfate that was sonicated before being baked, according to example embodiments.

FIG. 4 shows ΔE vs. exposure time to 100% H$_2$ sensing gas for disclosed embodiments including platinated BaSO$_4$, large scale BaSO$_4$ that was baked before sonication, and large scale BaSO$_4$ that was sonicated before being baked. It can be seen that again Pt doping the BaSO$_4$ supported PdO pigment increases the kinetics of the sensing reaction. FIG. 4 also shows at least for the large scale reactions performed, baking before sonication (e.g., 110° C. for 3 hours) increases the kinetics of the reaction as well as increasing the overall color change as compared to sonication before baking. It is believed that the energy given to the reaction during sonication is sufficient enough for dehydration of palladium hydroxide to palladium oxide in a 10 g BaSO$_4$batch, but for a larger support mass such as the 250 g BaSO$_4$ batch used in this Example an initial baking is needed for full conversion to palladium oxide.

Example 7

Figure 5:
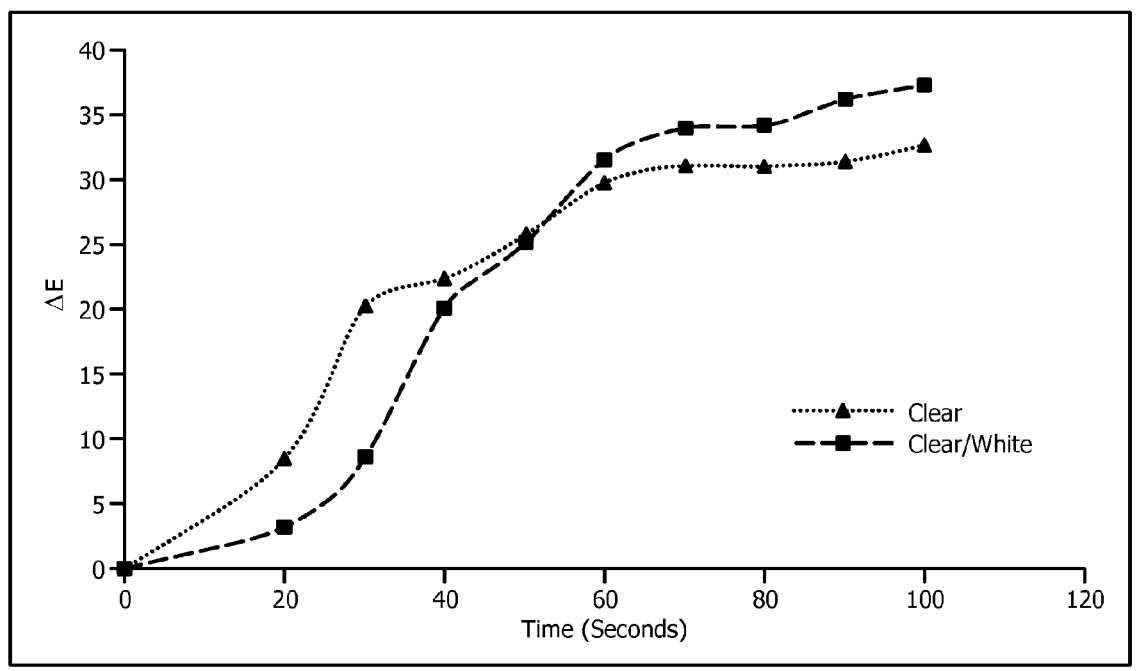
FIG. 5 shows $\Delta E$ vs. exposure time to 100% $H_2$ sensing gas for disclosed gas permeable polymer encapsulated BaSO$_4$ supported PdO chemochromic pigment samples which demonstrates excellent $\Delta E$ vs. time performance for both the clear and clear/white polymer embodiments.

BaSO$_4$/PdO 3 Wt % PdO Chemochromic Pigment Encapsulated in Clear/White Resin for Hydrogen Gas Detection BaSO$_4$ supported PdO pigments (BaSO$_4$/PdO 3 Wt % PdO) were mixed with Dow 734 silicone resins (a gas permeable polymer) to form an encapsulated $BaSO_4/PdO$ 3 Wt % PdO chemochromic pigment for hydrogen gas testing. 0.2 g of the pigment was ground with 0.8 mL octane, then 6.0 g of clear silicone and 0.7 g of white silicone was added and mixed thoroughly. The mixture was then drawn into a tape for use in detecting hydrogen gas. The ΔE vs. exposure time to 100% $H_2$ sensing gas shown in FIG. 5 demonstrates excellent ΔE vs. time performance for both the clear and clear/white disclosed encapsulated chemochromic pigment samples.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The invention claimed is:

1. An oxidation catalyst, comprising:
   a support comprising particles of an alkaline earth salt, and
   first particles comprising at least a palladium compound on said support, and
   a gas permeable polymer that provides a continuous phase that completely encapsulates said first particles and said support.

2. The oxidation catalyst of claim 1, wherein said alkaline earth salt comprises a sulfate, a carbonate, a hydroxide, an oxide, or a sulfide.

3. The oxidation catalyst of claim 1, wherein said alkaline earth salt comprises $BaSO_4$.

4. The oxidation catalyst of claim 1, wherein said palladium compound comprises palladium oxide, palladium hydroxide, or a palladium salt.

5. The oxidation catalyst of claim 1, wherein said first particles further comprise precious metal group (PMG) metal particles intermixed with particles of said palladium compound on said support.

6. The oxidation catalyst of claim 5, wherein said PMG metal particles comprise at least one of gold, silver and a platinum group metal.

7. The oxidation catalyst of claim 1, further comprising an ultraviolet (UV) absorber or UV blocker, or a mixture thereof on said support.

8. The oxidation catalyst of claim 7, wherein said UV blocker comprises zinc oxide or titania.

9. The oxidation catalyst of claim 7, wherein said UV absorber comprises a triazine compound, a benzophenone, or a benzotriazol.

10. The oxidation catalyst of claim 1, wherein said gas permeable polymer comprises silicone rubber or silicone resin.

11. An oxidation catalyst, comprising:
    a support comprising $BaSO_4$ particles, and
    first particles comprising PdO particles said support, and
    a gas permeable polymer that provides a continuous phase that completely encapsulates said first particles and said support.

12. The oxidation catalyst of claim 11, further comprising precious metal group (PMG) metal particles intermixed with said PdO particles on said support.

13. A method of forming an oxidation catalyst, comprising:
    providing a support comprising a plurality of particles of an alkaline earth salt
    depositing first particles comprising a palladium compound on said support while in a liquid phase including at least one solvent;
    removing said liquid phase to provide said oxidation catalyst, and
    forming a gas permeable polymer that provides a continuous phase that completely encapsulates said first particles and said support.

14. The method of claim 13, wherein said liquid phase is a slurry including said plurality of particles of said alkaline earth salt in said solvent, and said removing said liquid phase includes baking and then sonication after said baking.

15. The method of claim 13, wherein said alkaline earth salt comprises $BaSO_4$.

16. The method of claim 13, wherein said depositing said first particles comprises co-depositing said first particles together with precious metal group (PMG) metal particles to form mixed metal comprising particles.

17. The method of claim 16, wherein said PMG metal particles comprise at least one of gold, silver and a platinum group metal.

18. The method of claim 13, wherein said solvent comprises an alcohol and said depositing comprises sonication.

19. The method of claim 13, wherein said forming gas permeable polymer comprises:
    admixing a moisture or heat curable silicone sealant with said plurality of particles of said alkaline earth salt and said first particles, and
    curing said silicone sealant to form a rubbery gas permeable silicone polymer.

* * * * *